(12) United States Patent
Dougherty et al.

(10) Patent No.: US 7,635,761 B2
(45) Date of Patent: Dec. 22, 2009

(54) WATER-SOLUBLE GROUP III POLYETHER ACID SALT COMPLEXES AND THIN FILMS FROM SAME

(75) Inventors: T. Kirk Dougherty, Playa del Rey, CA (US); John J. Drab, Santa Barbara, CA (US)

(73) Assignee: Raytheon Company, Waltham, MA (US)

( * ) Notice: Subject to any disclaimer, the term of this patent is extended or adjusted under 35 U.S.C. 154(b) by 176 days.

(21) Appl. No.: 11/893,966

(22) Filed: Aug. 17, 2007

(65) Prior Publication Data

US 2007/0293661 A1 Dec. 20, 2007

Related U.S. Application Data

(62) Division of application No. 10/996,290, filed on Nov. 24, 2004, now Pat. No. 7,273,942.

(51) Int. Cl.
  *C07F 5/00* (2006.01)
  *C07F 5/06* (2006.01)
(52) U.S. Cl. .............................. 534/16; 556/1; 556/181; 556/183
(58) Field of Classification Search ..................... 556/1, 556/181, 183; 534/16
  See application file for complete search history.

(56) References Cited

U.S. PATENT DOCUMENTS

| | | | |
|---|---|---|---|
| 5,434,102 A | 7/1995 | Watanabe et al. | |
| 5,439,845 A | 8/1995 | Watanabe et al. | |
| 5,721,009 A | 2/1998 | Dougherty et al. | |
| 6,054,600 A * | 4/2000 | Dougherty et al. | 556/44 |
| 6,303,804 B1 * | 10/2001 | Dougherty et al. | 556/30 |
| 6,316,651 B1 * | 11/2001 | Dougherty et al. | 556/30 |
| 6,322,890 B1 | 11/2001 | Barron et al. | |
| 7,119,217 B2 * | 10/2006 | Jiang et al. | 556/1 |
| 7,273,942 B1 * | 9/2007 | Dougherty et al. | 556/1 |
| 2002/0068761 A1 * | 6/2002 | Bernstein | 514/460 |
| 2004/0191328 A1 * | 9/2004 | Warrell et al. | 424/617 |
| 2005/0168916 A1 * | 8/2005 | Dougherty et al. | 361/321.1 |

FOREIGN PATENT DOCUMENTS

WO    WO 93/12538    6/1993

OTHER PUBLICATIONS

Narayanan et al. Synthesis of soluble aluminium carboxylates directly from aluminium hydroxide. Jour. Mat. Chem. (2000), 10(9), 2097-2104.*
Vest, G.M. et al, Synthesis of Metallo-Organic Compounds for Mod Powders and Films, Mat. Res. Soc. Symp. Proc., vol. 60, pp. 35-42, (1986).
J.V. Mantese, et al., Metalorganic Deposition (MOD): A Non Vacuum, Spin-on, Liquid-Based, Thin Film Method, MRS Bulletin, pp. 48-53, (Oct. 1989).
Takashi Kojima, et al., Ferroelectric Properties of Lanthanide-substituted Bi4Ti3O12 epitaxial thin films grown by metalorganic chemical vapor deposition, Journal of Applied Physics, pp. 1707-1711 (Feb. 1, 2003).
Dinghua Bao, et al., Structural and Electrical characteristics of chemical-solution-derived (Bi,La)4Ti3O12 thin films with various Bi2O3 template layers, Journal of Applied Physics, pp. 497-503 (Jan. 1, 2003).
B.H. Park, et al., Lanthanum-substituted bismuth titanate for use in non-volatile memories, Nature, vol. 401, www.nature.com , pp. 682-684, (Oct. 14, 1999).
Rhonda L. Callender, et al., Aqueous Synthesis of Water-Soluble Alumozanes: Environmentally Benign Precursors to Alumina and Aluminum-Based Ceramics, Chem.Mater., vol. 9, pp. 2418-2433, (1997).
A.W. Apblett, et al., Phosphorous, Sulfur and Silicon, vol. 98-94, pp. 481-482 (1994). Metal Organic Precursors for Yttria.

* cited by examiner

*Primary Examiner*—Porfirio Nazario Gonzalez
(74) *Attorney, Agent, or Firm*—Leonard A. Alkov

(57) ABSTRACT

A water-stable and water-soluble ceramic precursor is provided, containing at least one Group III element. Also, a metal acid salt complex is provided comprising (1) bismuth, lanthanum, and titanium, and (2) a polyether acid. In addition, methods are provided for preparing the Group III metal acid salt complex and the Bi, La, Ti acid salt complex comprising a bismuth polyether acid salt complex, a lanthanum polyether acid salt complex, and a titanium polyether acid salt complex. Finally, devices that include lanthanum-doped bismuth titanate as the active component are provided, as well as a water-stable and water-soluble gallium polyether acid complex.

6 Claims, 1 Drawing Sheet

WATER-SOLUBLE GROUP III POLYETHER ACID SALT COMPLEXES AND THIN FILMS FROM SAME

CROSS REFERENCE TO RELATED APPLICATION

This application is a Divisional Application of U.S. patent application Ser. No. 10/996,290, filed Nov. 24, 2004, now U.S. Pat. No. 7,273,942, issued Sep. 25, 2007, by T. Kirk Dougherty and John J. Drab and is hereby incorporated by reference herein in its entirety.

TECHNICAL FIELD

The present invention relates generally to improved ceramic precursors and specifically to ceramic precursors for fabricating Group III soluble ceramic precursor materials useful for making thin films, coatings, thick films and bulk ceramic materials, as well as polyether acid gallium materials which have interest for oral delivery of gallium which has been shown to be a therapeutic agents for certain cancers and to protect bone.

BACKGROUND ART

Group III-based ceramic materials have a variety of uses. Examples of Group III materials include (1) alumina ($Al_2O_3$), (2) ferroelectric lanthanide-containing materials, such as bismuth lanthanum titanate (BLT), and (3) gallium compounds.

In particular, of concern are the synthesis, processing, and fabrication of the Group III-based materials into thin film is, coatings, thick films, and bulk ceramic materials for, e.g., electronic devices and, in the case of gallium, for oral delivery (gallium has been shown to be a therapeutic agent for certain cancers and for protecting bone).

Metal-organic decomposition (MOD) deposition processes are known for a number of ceramic materials. The MOD process typically involves the synthesis of thin film ceramics from metal organic acid salts (mostly aliphatic acids such as neo-decanoic acid or 2-ethylhexanoic acid). The MOD process is described in, for example, (1) U.S. Pat. No. 5,721,009, "Controlled Carbon Content MOD Precursor Materials Using Organic Acid Anhydride", issued to Thomas K. Dougherty et al on Feb. 24, 1998; (2) J. V. Mantese et al, "Metalorganic Deposition (MOD): A Nonvacuum, Spin-on, Liquid-Based, Thin Film Method", *MRS Bulletin*, pp. 48-53 (October 1989); (3) WO 93/12538, "Process for Fabricating Layered Superlattice Materials", filed in the names of Carlos A. Paz de Araujo et al, published on 24 Jun. 1993; (4) U.S. Pat. No. 5,434,102 (issued on Jul. 18, 1995) and U.S. Pat. No. 5,439,845 (issued on Aug. 8, 1995), to Hitoshi Watanabe et al and both entitled "Process for Fabricating Layered Superlattice Materials and Making Electronic Devices Including Same"; and (5) G. M. Vest et al, "Synthesis of Metallo-Organic Compounds for MOD Powders and Films", *Materials Research Society Symposium Proceedings*, Vol. 60, pp. 35-42 (1986).

The present inventors and associates have continued their work in this area, culminating in (1) U.S. Pat. No. 6,054,600, "Non-Toxic Solvent Soluble Group IV and V Metal Acid Salt Complexes Using Polyether Acid Anhydrides", issued to T. Kirk Dougherty et al on Apr. 25, 2000; (2) U.S. Pat. No. 6,303,804, "Environmentally Benign Bismuth-Containing Spin-on Precursor Materials", issued to T. Kirk Dougherty et al on Oct. 16, 2001; (3) U.S. Pat. No. 6,316,651, "Environmentally Benign Group II and Group IV or V Spin-on Precursor Materials", issued to T. Kirk Dougherty et al on Nov. 13, 2001, and (4) application Ser. No. 10/771,066, filed Feb. 2, 2004. The contents of these patents and patent application are incorporated herein by reference.

Similar alumina-forming polyether acid materials have been described by Barron in, for example, U.S. Pat. No. 6,322,890, and *Chem. Mater.*, Vol. 9, pp. 2418-2433 (1997) useful as ceramic binders and fillers and as polymerization catalysts. In this case, the materials are formed by a high temperature reaction of the free acids with alumina minerals that takes a long time. Thus, the materials of Barron do not appear to be as easy to make, as soluble or as easy to characterize and process as the alumina materials as described herein.

Lanthanum-doped bismuth titanate (BLT) is a newer ferroelectric material that has recently been developed. BLT prior art includes Park et al, *Nature*, Vol. 401, pp. 682-684 (October 1999); Bao et al, *J. Appl. Phys.*, Vol. 93(1), pp. 497-503 (1 Jan. 2003); and Kojima et al, *J. Appl. Phys.*, Vol. 93(3), pp. 1707-1712 (1 Feb. 2003).

Of note is a single reference for the yttria precursors of the polyether acids, namely, Apblett et al in *Phosphorous, Sulfur and Silicon*, Vol. 93-94, pp. 481-482 (1994).

Finally, gallium maltolate is being investigated as a water-stable and soluble oral delivery mechanism for gallium. The use of gallium organic salts for therapeutic uses is desirable if these materials can be made easier to synthesize and characterize than presently. Further, it would be desirable to tailor the gallium compounds as to bioavailability.

Thus, there remains a need for a soluble Group III containing precursor which is compatible and soluble in non-toxic and environmentally benign solvents (including water), has unlimited stability and shelf life, and provides high quality Group III-containing films and materials.

DISCLOSURE OF INVENTION

In accordance with the present invention, a water-stable and water-soluble ceramic precursor is provided, containing at least one Group III element.

Further in accordance with the present invention, a metal acid salt complex is provided comprising (1) lanthanum, bismuth, and titanium, and (2) a polyether acid.

Still further in accordance with the present invention, a method of preparing a Group III metal acid salt complex is provided. The method comprises either:

combining at least one Group III metal salt and a polyether acid; or combining (1) at least one Group III metal alkoxide, (2) a polyether acid anhydride, and, optionally, (3) a polyether acid.

Yet further in accordance with the present invention, a process is provided for preparing a metal acid salt complex comprising a bismuth polyether acid salt complex, a lanthanum polyether acid salt complex, and a titanium polyether acid salt complex, the process comprising:

preparing the bismuth polyether acid salt complex;

preparing the lanthanum polyether acid salt complex;

preparing the titanium polyether acid salt complex; and combining the bismuth polyether acid salt complex, the lanthanum polyether acid complex, and the titanium polyether acid salt complex.

Still further in accordance with the present invention, a device is provided that includes lanthanum-doped bismuth titanate as its active component, the lanthanum-doped bismuth titanate prepared using a ceramic precursor that contains at least one metal polyether acid salt complex.

Yet further in accordance with the present invention, a device is provided that includes lanthanum-doped bismuth titanate as its active component, the lanthanum-doped bismuth titanate prepared using a metal acid salt complex comprising (1) lanthanum, bismuth, and titanium, and (2) a polyether acid.

Further in accordance with the present invention, a water-stable and water-soluble gallium polyether acid complex is provided.

BRIEF DESCRIPTION OF THE DRAWINGS

The sole FIGURE is a plot on coordinates of polarization (in $\mu C/cm^2$) and voltage (in V), depicting the hysteretic properties of a bismuth lanthanum titanate thin film ferroelectric capacitor, prepared in accordance with the teachings herein.

BEST MODES FOR CARRYING OUT THE INVENTION

Figure 1:
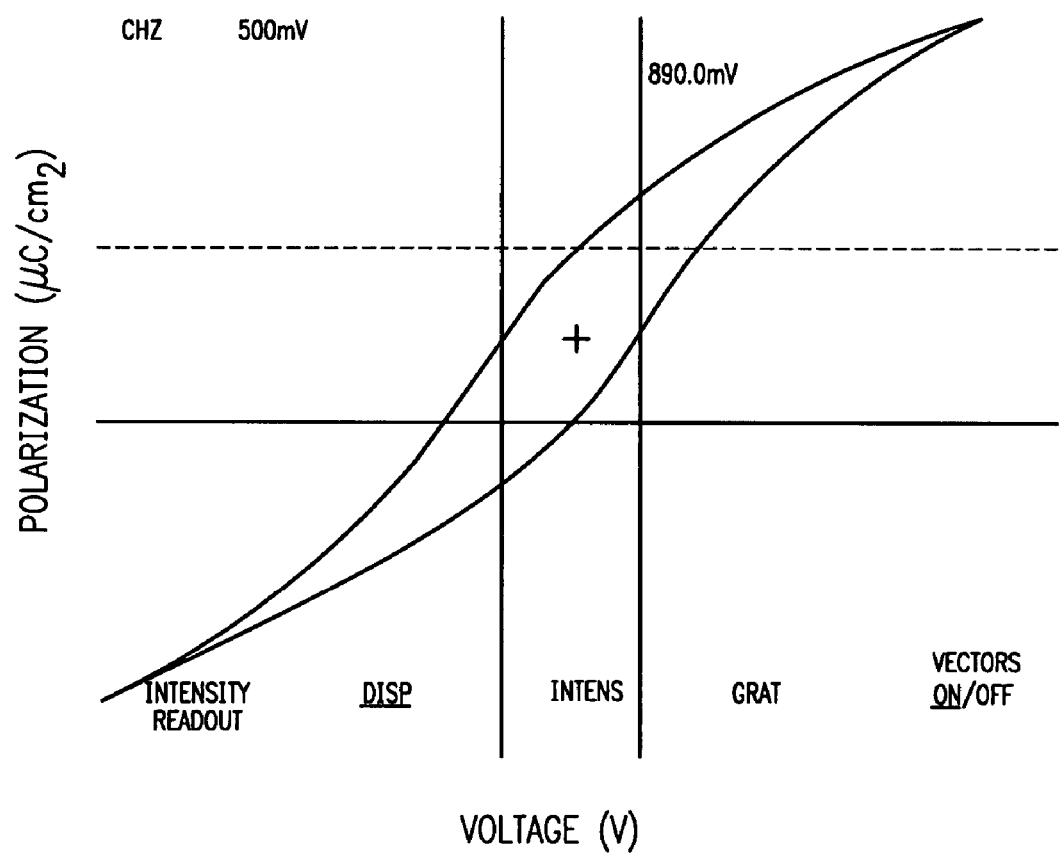

The present invention is directed to the synthesis, processing and fabrication into thin film electronic devices of several Group III soluble ceramic precursor materials useful for making thin films, coatings, thick films and bulk ceramic materials. Examples include alumina and the ferroelectric lanthanide containing materials, a specific example of which is bismuth lanthanum titanate (BLT). The materials are water-stable and water-processable and have a high solids content as compared to the prior art materials. Also described are polyether acid gallium materials which have interest for oral delivery of gallium which has been shown to be a therapeutic agent for certain cancers and to protect bone.

The present invention is a continuation of the present inventors' work in water-stable and processable ceramic precursors materials best exemplified by above-referenced U.S. Pat. No. 6,054,600, which discloses and claims the formation of Group IV and V materials. The present disclosure describes the Group III materials and their use in, for example, the production of ferroelectric thin films in the case of lanthanum. The present disclosure also describes the aluminum precursors that yield alumina thin films, coatings and bulk ceramics. The present invention provides a more convenient and chemically controlled entry to these precursors and is more general throughout the Group III materials, which provide a more processable form of aluminum precursors as compared to the Barron derivatives.

The present invention describes the use of the specific polyether acid metal salts of aluminum, lanthanum and gallium and in general the Group III metals. These materials have uses both in new electronic material applications and devices and the systems which use them. In addition, the materials described herein may offer additional advantages and new entries to water-soluble complexes for these elements. For example, water-soluble gallium compounds are of interest as, for example, oral therapeutic agents for cancer and other maladies.

Thus, utility of the entire set of patents is much more general than the current use for electronic devices, and these Group III materials improve upon the prior art in a broad range of applications.

The present invention provides the Group III elements in water-soluble and stable form, providing:

1. Lanthanum, and analogously the entire lanthanide group, as new ceramic precursors useful as ferroelectric thin films.
2. Aluminum, and thus the alumina precursors, useful as coatings (for example, optical coatings), thin films, and as binders and processing aids for bulk alumina ceramics (alumina being one of the more widely used bulk ceramics).
3. Gallium, and water-soluble gallium compounds, which are being investigated as a cancer therapeutic agents.

These water-soluble and stable elemental materials may provide a number of other therapeutic agents, depending on the stability and bioavailability of the materials. It maybe the case that the chemical tailoring available by use of the different size polyether acid ligands may be used to tune the bioavailability.

Formulae (I)-(III) below depict three generic Group III compounds, where M is a Group III metal. In the case of M=Ga, these compounds may have tuned stability and transport properties across bio membranes.

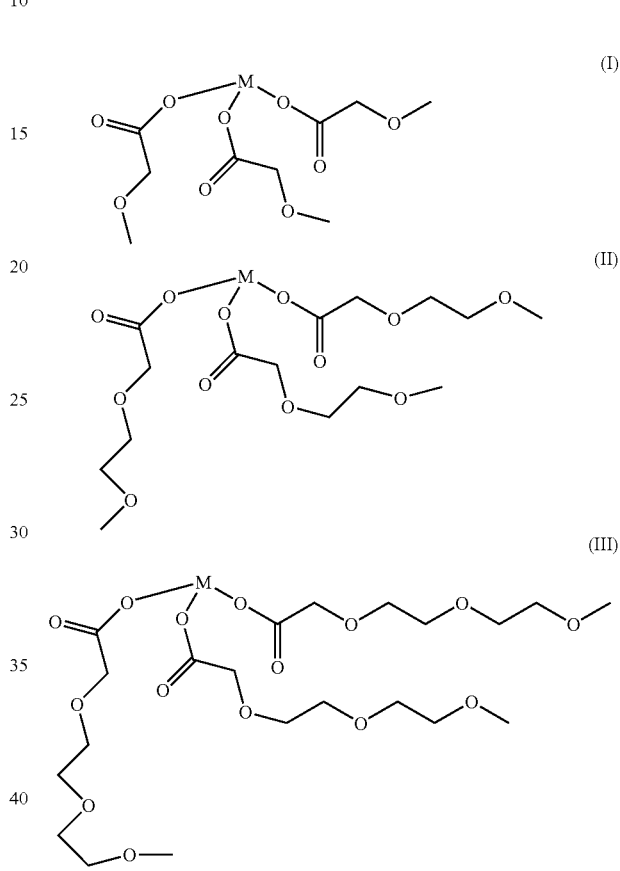

Applications for these ceramic precursor materials include, but are not limited to, ferroelectric memories, Group III-containing materials, binders, and reactive fillers in ceramic processing, other thin and thick film devices, and anywhere where water-stable ceramic (or mineral) precursors might see use.

The present invention provides for the Group III materials compatible with less toxic solvents useful for manufacture of these and other products as well as new products.

In one embodiment, BLT (lanthanum-doped bismuth titanate) thin films are provided, which may be used in ferroelectric memories.

Applicants have also prepared a water-soluble alumina precursor, which is an important new material which is easier to make, better controlled and characterizable and has improved processing and solubility characteristics than the Barron materials described above.

In accordance with the present invention, Group III metal acid salt complexes are provided comprising a complex of at least one Group III metal alkoxide and a polyether acid. The Group III metal acid salt complexes are prepared by either (a) combining the Group III salt(s) with a polyether acid or (b) combining the Group III metal alkoxide(s), a polyether acid anhydride, and, optionally, the polyether acid.

The present invention is directed to the use of (a) the metal salts of Group III elements, e.g., Al, Ga, In, Tl, Sc, Y, La, the lanthanides, Ac, and the actinides, and other metals with a polyether acid and (b) the metal alkoxides of the Group III elements and other metals with a polyether acid anhydride (plus, optionally, the polyether acid) to produce new ceramic precursors and materials and devices therefrom.

Examples of the metal salts include, but are not limited to, the simple organic metal salts, such as the corresponding acetates, carbonates, and hydroxides. Examples of the metal alkoxides include, but are not limited to, the lower metal alkoxides, such as methoxides, ethoxides, propoxides, and butoxides.

Essentially, the polyether acids useful in the practice of the present invention are polyethers of ethylene glycol, having the formula

where n is 0 to 2.

The Group III polyether acid salt complex is represented by the following structure

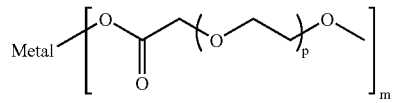

where "Metal" is selected from a Group III element (as listed above), m is 3, and p is independently 0, 1 or 2 for each of the three ligands.

Mixed metal acid salt complexes are also contemplated herein, such as mixtures of bismuth, lanthanum, and titanium for fabricating BLT thin film ferroelectric memories. In that case, m is 3 for both bismuth and lanthanum and is 4 for titanium. For titanium, there thus are four ligands, and p is 0, 1 or 2 for each of the four ligands.

Examples of the polyether acids used to make the polyether acid anhydride include, but are not limited to, methoxyacetic acid, ethoxyacetic acid, methoxyethoxyacetic acid, and methoxyethoxyethoxyacetic acid.

The solvents preferably used in formulating the complexes include, but are not limited to, 2-propanol and water, which are considerably less toxic than xylenes and n-butyl acetate often used. However, other polar, non-toxic solvents, such as low molecular weight alcohols, may also be employed in the practice of the present invention. The low molecular weight alcohols have no more than five carbon atoms.

The general synthetic route to preparing metal acid salt complexes from metal salts and polyether acid is as follows:
1. Combine the metal salt(s) with the polyether acid.

The metal salt used may comprise any of the known salts for that metal, including, but not limited to the salts listed above, namely, acetate, carbonate, or hydroxide.

The general synthetic route to preparing metal acid salt complexes from metal alkoxide complexes is as follows:
1. Prepare the polyether acid anhydride from the corresponding polyether acid by combining the polyether acid with a dehydrating agent; and
2. Combine the polyether acid anhydride and the metal alkoxide. In some embodiments, it may be desirable to also include the corresponding polyether acid in the mixture.

The dehydrating agent used in the first reaction may comprise any of the known dehydrating agents used to convert organic acids to the corresponding anhydride. Examples include, but are not limited to, acetic anhydride and dicyclohexylcarbodiimide.

The metal alkoxide used in the second reaction may comprise any of the known alkoxides for that metal.

The aluminum polyether acid salt complexes of the present invention are provided by reacting an aluminum alkoxide material (in a specific example, the aluminum sec-butoxide) with a polyether acid anhydride. Similar alumina-forming polyether acid materials have been described by Barron, as mentioned above. In the Barron work, the materials are formed by lengthy and high temperature reaction of the free acids with alumina minerals and as described by Barron are alumoxanes, which are aluminum oxygen cage materials with various polyether acid ligands attached that are difficult to fully characterize. Thus, the materials of Barron are not as easy to make, as soluble or as easy to characterize and process as the alumina materials as described in the present invention.

EXAMPLES

Synthesis of Aluminum(III)-Methoxyacetate-Methoxyethoxyacetate

To aluminum-s-butoxide (182.4 grams, 0.74 mol, Geleste AKA020) was added a mixture of methoxyacetic anhydride (124 grams, 0.76 mol) and methoxyethoxyacetic anhydride (292 grams, 1.17 mol). After stirring at room temperature for twenty minutes, the reaction mixture was heated to 150° C., stirred for 30 min. and allowed to stir and cool overnight. The next day, the liquid reaction mixture was concentrated on a rotary evaporator to yield the product as a water stable and completely miscible amorphous solid (287 grams of material, 6.96% Al calc.). Found 13% alumina as measured by TGA (thermogravimetric analysis), calc. 13.14%. IR (thin film) 3432, 3056, 2970, 2908, 2389, 2113, 1960 cm$^{-1}$.

Synthesis of Gallium(III)-Methoxyacetate

To gallium ethoxide (1.56 gram, 0.0076 mol, AlfaAesar 41907) was added methoxyacetic anhydride (3.7 gram, 0.0228 mol, made by the reaction of methoxyacetic acid and acetic anhydride). The contents of the reaction mixture were heated to 60° C. for 16 hours to give a viscous liquid mixture of the product and the by-product the ethylester of methoxyacetic acid. The mixture was soluble and stable in water and methanol. The product mixture left a 10.14% ceramic oxide residue as measured by TGA in air.

Synthesis of Gallium(III)-Methoxyethoxyacetate

To gallium ethoxide (1.06 gram, 0.00517 mol, AlfaAesar 41907) was added methoxyethoxyacetic anhydride (4.16 gram, 0.0167 mol, made by the reaction of methoxyethoxyacetic acid and acetic anhydride). The contents of the reaction mixture were heated to 60° C. for 18 hours to give a viscous liquid mixture of the product and the by-product the ethylester of methoxyethoxyacetic acid. The mixture was soluble and stable in water and in dilute aqueous hydrochloric acid. The product mixture containing the ester and gallium salt left a 6.09% ceramic oxide residue as measured by TGA in air. IR (thin film) 2984, 2931, 2894, 1753,1603, 1457, 1204, 1145, 1101 cm$^{-1}$.

Synthesis of Lanthanum(III) Methoxyethoxyacetate

To lanthanum acetate (45.103 gram, 0.13 mol, AlfaAesar 11263) was added methoxyethoxyacetic acid (129.7 gram, 0.97 mol, Aldrich 40,701-1). The contents of the reaction mixture were magnetically stirred and heated to 145° C. and then the by-product acetic acid as well as some of the excess ether acid were removed by distillation to give the product (144.3 gram, 12.6% lanthanum) in methoxyethoxy acetic acid. TGA analysis of the material showed a ceramic oxide yield of 13.25%; calc 14.8%. IR (thin film) 2931, 2896, 1739, 1588, 1457, 1429, 1144, 1118 cm$^{-1}$.

Synthesis of Neodymium(III)-Methoxyacetate

To neodymium carbonate hydrate (10.606 gram, 0.023 mol, AlfaAesar 15301) were added methoxyacetic acid (20.0 gram, 0.22 mol, Aldrich 194557) and deionized water (6.0 gram). The contents of the reaction mixture were magnetically stirred and heated to 90° C. for 14 hours. Evolution of gas (presumably $CO_2$) was copious on heating and care should be taken on running similar reactions on a larger scale. The next day, the reaction contents were cooled to give the product in a solution of free acid and water. (32.0 gram, 10.3% neodymium). TGA analysis of the material showed a ceramic oxide yield of 14.86%. IR (thin film) 3007, 2946, 1735, 1592, 1427, 1341, 1246, 1202, 1121 cm$^{-1}$.

Formulation of Bismuth and Lanthanum and Titanium(IV)-3,6-Dioxaheptanoate to a Water-Processable and Non-Toxic Solvent-Containing Precursor to Lanthanum-Doped Bismuth Titanate (BLT)

A BLT precursor solution was made by combining 10.08 gram of a solution of bismuth methoxyethoxy acetate (23.9% bismuth made by the reaction of the free acid and triphenyl bismuth); 3.597 grams of the lanthanum methoxyethoxy acetate described above; and 13.82 grams of solution of titanium methoxy acetate (3.99% Ti). The synthesis of triphenyl bismuth is disclosed in above-referenced U.S. Pat. No. 6,303,804, while the synthesis of titanium methoxy acetate is disclosed in above-referenced U.S. Pat. No. 6,316,651. The BLT precursor solution having a gram-atom ratio of Bi:La:Ti of 3.35:0.85:3.00 was used to make the thin film BLT ferroelectric capacitors described immediately below.

Processing of Described BLT Precursor to BLT Thin Films

1. Substrate Preparation Including Bottom Electrode Evaporation.

A conventional 20 mil thick silicon wafer was prepared with 5,000 Å of a wet thermal oxide (silicon). A 25 Å thick Ta adhesion layer followed by a 1,800 Å thick Pt layer were E-beam evaporated onto the substrate. Sheet resistance of the electrodes was 0.73 ohm/square. The electrodes were pre-annealed in oxygen for 30 min at 650° C. to oxidize the Ta layer and stabilize the Pt layer.

2. Deposition and Firing of Bismuth Lanthanum Titanate Thin Film on Electroded Substrate.

Wafers were coated with the BLT solution described above using a 3 to 5 Krpm 30 sec spin. After coating, the wafers were slowly lowered onto a 320° C. hot plate and baked for 4 minutes.

After spin coating and hot plate baking, the wafers were fired in a mini-brute furnace in flowing $O_2$ at 700° C.

After firing, the wafers showed no signs of cracking and no adhesion failures. SEM analysis of the dielectric films showed the surface to be smooth. Thickness measurements showed the thickness to be approximately 1,100 to 1,700 Å.

3. Application of Top Electrode.

A 1,000 Å Pt top electrode was deposited through a shadow mask using varying top electrode sizes of approximately 10, 15, 20, 40, 80, and 160 mil diameter. The stack was annealed at 700° C. for 2 hours before electrical test.

4. Initial Electrical Test.

The devices were tested on an analytical prober. Contact to the top electrode was made directly with a probe tip, contact to the bottom electrode was made by scratching through the BLT layer with a second probe tip. The CV characteristics were measured using a HP4275A LCR meter at 100 KHz using a modulation voltage of 35 mV over a wide range of bias voltages. The IV characteristics were measured using a HP 4145B Semiconductor Parameter Analyzer over the range of −3.5 V to +3.5 V. For a typical 10 mil diameter shadow mask capacitor, the capacitance ranged from 1.69 pF at 0 V to 0.75 pF at 6.5 V. The maximum leakage current was measured to be 100 nA at 3.5 V. The devices exhibited the characteristic hysteresis effects of ferroelectric materials, as shown in the sole Figure, which is a plot on coordinates of polarization and voltage.

SUMMARY

A number of Group III polyether acid ceramic precursor materials and thin film BLT ferroelectric capacitors made from these materials have been disclosed.

INDUSTRIAL APPLICABILITY

The formation of Group III polyether acid ceramic precursor materials is expected to find use in the fabrication of a number of solid state devices, including, but not limited to, ferroelectric devices, as well as in the fabrication of water-soluble gallium complexes.

What is claimed is:

1. A method of preparing a Group III polyether acid salt complex, said method comprising combining (1) at least one Group III metal alkoxide, (2) a polyether acid anhydride, and, optionally, (3) a polyether acid.

2. The method of claim 1 wherein said Group III metal alkoxide comprises a lower alkoxide of a Group III metal.

3. The method of claim 2 wherein said lower alkoxide is selected from the group consisting of methoxide, ethoxide, propoxide, and butoxide.

4. The method of claim 1 wherein said polyether acid anhydride is prepared from the corresponding polyether acid by combining said polyether acid with a dehydrating agent.

5. The method of claim 1 wherein said polyether acid is given by the formula

where x is an integer of 0 to 2.

6. The method of claim 5 wherein said Group III polyether acid salt complex is represented by the following structure

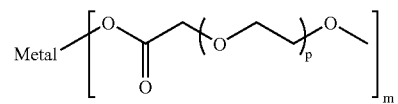

where "Metal" is selected from the Group III elements, m is 3, and p is independently 0, 1 or 2 for each of the three ligands.

* * * * *